United States Patent
Gimbel

(10) Patent No.: US 11,054,366 B2
(45) Date of Patent: Jul. 6, 2021

(54) INFRARED OPTICAL GAS-MEASURING DEVICE

(71) Applicant: Dräger Safety AG & Co. KGaA, Lübeck (DE)

(72) Inventor: Doreen Gimbel, Lübeck (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 377 days.

(21) Appl. No.: 16/178,011

(22) Filed: Nov. 1, 2018

(65) Prior Publication Data
US 2019/0128800 A1   May 2, 2019

(30) Foreign Application Priority Data

Nov. 2, 2017   (DE) .................. 10 2017 010 151.5

(51) Int. Cl.
| | |
|---|---|
| *G01N 21/3504* | (2014.01) |
| *G01N 33/00* | (2006.01) |
| *H04N 5/247* | (2006.01) |
| *H04N 5/33* | (2006.01) |
| *G01N 21/17* | (2006.01) |

(52) U.S. Cl.
CPC ..... *G01N 21/3504* (2013.01); *G01N 33/0004* (2013.01); *H04N 5/247* (2013.01); *H04N 5/33* (2013.01); *G01N 2021/1765* (2013.01); *G01N 2021/3531* (2013.01)

(58) Field of Classification Search
USPC ........................................................ 702/24
See application file for complete search history.

(56) References Cited

U.S. PATENT DOCUMENTS

| | | |
|---|---|---|
| 4,866,594 A | 9/1989 | David et al. |
| 5,656,813 A | 8/1997 | Moore et al. |
| 6,130,964 A | 10/2000 | Marques et al. |
| 6,297,504 B1 * | 10/2001 | Andreou ............. G01J 3/453 |
| | | 250/330 |
| 6,803,577 B2 | 10/2004 | Edner et al. |
| 6,904,347 B1 | 6/2005 | Berenz et al. |
| 7,646,987 B2 | 1/2010 | Killinger |
| 7,769,236 B2 | 8/2010 | Fiala |

(Continued)

FOREIGN PATENT DOCUMENTS

| | | |
|---|---|---|
| DE | 4 414 434 A1 | 11/1995 |
| EP | 0 443 064 B1 | 11/1994 |

(Continued)

*Primary Examiner* — Paul D Lee
(74) *Attorney, Agent, or Firm* — McGlew and Tuttle, P.C.

(57) ABSTRACT

A device (1) for gas measurement in a measuring environment (7) with a first camera (3) configured to detecting an invisible image area (33) in the measuring environment (7) and with a second camera (5) configured to detecting a visible image area (55) in the measuring environment (7). A control unit (13) initiates a detection of invisible image information (33') within at least one detection area (11, 33, 55) and a detection of visible image information (55') in the detection area (11, 33, 55). The control unit (13) determines special image areas (66), which indicate individual persons (9) or a plurality of persons (9). The control unit (13) is configured to determine at least one gas concentration (21') on the basis of the image information (33'), taking into account the special image areas (66).

10 Claims, 1 Drawing Sheet

(56) References Cited

U.S. PATENT DOCUMENTS

| | | | |
|---|---|---|---|
| 7,977,639 B2 | 7/2011 | Maillart et al. | |
| 8,300,949 B2 | 10/2012 | Xu | |
| 8,520,970 B2 | 8/2013 | Strandemar | |
| 8,755,597 B1 | 6/2014 | Tantalo et al. | |
| 8,803,093 B2 | 8/2014 | Joensson | |
| 2013/0321637 A1* | 12/2013 | Frank | H04N 5/2257 348/152 |
| 2014/0002639 A1 | 1/2014 | Cheben et al. | |
| 2018/0136072 A1* | 5/2018 | Cabib | G01N 21/3504 |
| 2019/0003919 A1* | 1/2019 | Asano | G01M 3/02 |

FOREIGN PATENT DOCUMENTS

| | | |
|---|---|---|
| WO | 2008 145 592 A1 | 12/2008 |
| WO | 2015 011 423 A1 | 1/2015 |
| WO | 2015 166 265 A1 | 11/2015 |

\* cited by examiner

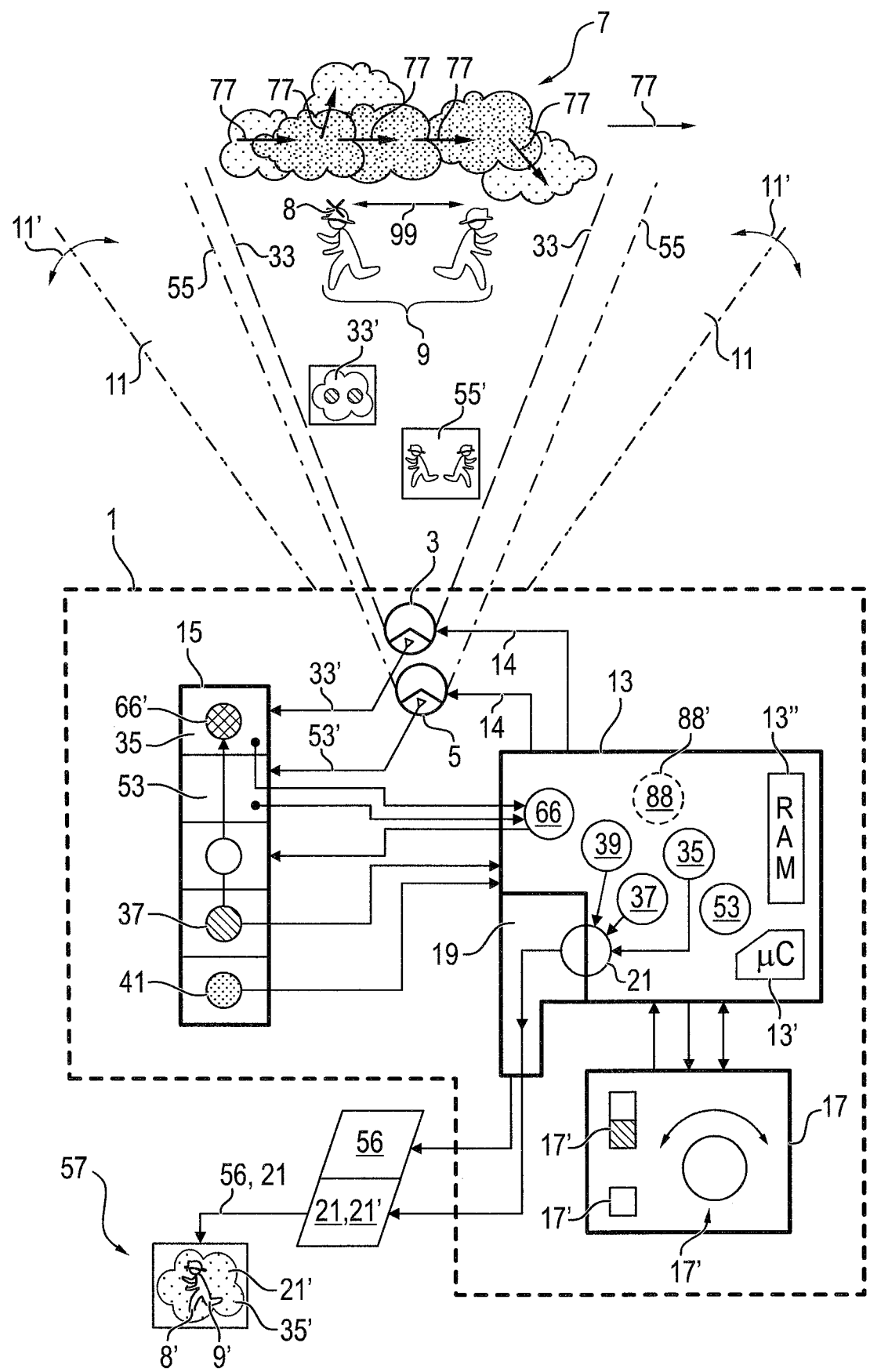

INFRARED OPTICAL GAS-MEASURING DEVICE

CROSS REFERENCE TO RELATED APPLICATIONS

This application claims the benefit of priority under 35 U.S.C. § 119 of German Application 10 2017 010 151.5, filed Nov. 2, 2017, the entire contents of which are incorporated herein by reference.

TECHNICAL FIELD

The present invention deals with the subject of how an infrared optical gas measurement can be configured in terms of the measurement results with improved reliability in a measuring environment in a scenario with locally changing quantities of a measured gas and with persons present and moving in the measuring environment.

BACKGROUND

In larger areas of industrial plants, in which the discharge of gases, aerosols or vapors, for example, from pipeline systems, is possible and gas clouds may thus form from the discharged gas, it is necessary and useful to detect such gas clouds by means of suitable monitoring systems in order to guarantee occupational safety, work safety and the health of the employees working in these plants. For example, so-called stationary gas warning units, comprising a plurality of measuring devices, which are equipped, for example, with catalytic infrared optical or electrochemical gas sensors or semiconductor sensors, and which are placed at different measuring locations in the industrial area, are suitable for this in conjunction with a central analysis system. A gas warning unit of such a configuration is described, for example, in U.S. Pat. No. 4,866,594 A.

Another possibility for monitoring an area for gas clouds is possible with a so-called "laser open path" system, as it is described in U.S. Pat. No. 7,646,987 B2. The presence of a target gas, which passes through the directed laser beam, can be detected by means of a directed infrared laser bream with a corresponding detector, by means of gas species-specific IR absorption, because the infrared radiation falls on the detector with reduced light intensity in the presence of the target gas.

The presence of gas clouds in an environment as well as the local and spatial changes of such gas clouds can be detected by means of a so-called gas camera. A gas camera is able, for example, to detect a heat radiation from objects and gas clouds in a measuring environment as an infrared radiation, i.e., to generate a thermographic image of the measuring environment.

Gas camera systems are known, for example, from WO 2015 166 265 A1, U.S. Pat. No. 5,656,813 A or U.S. Pat. No. 8,803,093 B2.

WO 2015 011 423 A1 describes the detection of local changes or movements of gas clouds in an area. Thermographic camera systems are able to detect gas concentrations as well as gas concentration distributions and changes thereof, for example, of gas clouds before a scenario, which is formed by the measuring environment, i.e., the area of the industrial plant. Changes in the foreground of the image, for example, due to the movement of vehicles, such as tank trucks, may lead to an at least temporary impairment of the function of determining the gas concentration, because these may hide the gas cloud in the field of view of the gas camera.

Portable gas camera systems may also be used to temporarily secure work assignments, for example, of working groups, which carry out installation or repair activities on tank or pipeline systems. A gas camera can be used and positioned portably for this in order to secure the location of the work assignment by measurements, for example, in order to monitor the gas concentrations of certain target gases by measurement in a local area around the work assignment location in order to warn the workers of the working group in time when a gas cloud is approaching.

It is problematic in connection with such a mobile use of a gas camera that the workers of the working group are within the area of the measuring environment of the gas camera and are thus part of the image foreground during the detection of the gas concentrations as well as of the gas concentration distributions and of the changes in these concentration distributions in the gas clouds. Since the workers of the working group usually move while performing their activities in the measuring environment, a problem arises because measuring situations may arise in which the work assignments are not secured continuously, because these persons could possibly hide a gas cloud. It is useful for reliably securing the measuring environment or the area in which the work assignment is carried out to detect whether and where a person or a plurality of persons is/are located at the work assignment location, especially in the image foreground.

Thus, DE 4 414 434 A1 describes a use of a camera with image analysis for an application for detecting a person on a conveyor belt in the field of mining technology.

The detection of persons from the area around vehicles is known, for example, from U.S. Pat. No. 6,904,347 B1 or WO 2008 145 592 A1. U.S. Pat. No. 6,904,347 B1 describes how the presence and the position of a human occupant of a vehicle is detected by means of an infrared detector in order to initiate or not to initiate the deployment of an air bag in case of an accident as needed. WO 2008 145 592 A1 describes a biometric identification of persons in the vehicle with determination of personal data with a provision of personal data for use in an emergency call in case of an emergency.

SUMMARY OF THE INVENTION

Based on this state of the art, an object of the present invention is to improve the reliability of an infrared optical gas-measuring device.

A device according to the present invention for gas measurement in a measuring environment has a first camera, which is suitable for the infrared detection of an invisible image area in the measuring environment. The device according to the present invention for gas measurement in a measuring environment has a second camera suitable for detecting a visible image area in the measuring environment. The device according to the present invention for gas measurement in a measuring environment further has a control unit, an operating unit, an output unit and a data storage unit.

The first camera may be configured, for example, as a camera or also as a measuring detector or as a point detector for detecting light in the invisible infrared optical spectral range, i.e., in a spectral range that can be defined by wavelengths of $\lambda=0.78$ μm to 14.0 μm. The first camera may be configured, for example, as a stationary or mobile thermographic or infrared optical monitoring camera for continuous space or area monitoring.

The second camera may be configured, for example, as a camera for detecting light in the visible optical spectral range, i.e., in a spectral range that can be defined by wavelengths of $\lambda=0.4$ μm to 0.78 μm. Embodiments of the second camera may be, for example, stationary or mobile visual monitoring cameras or also so-called web cams for continuous space or area monitoring.

The control unit is usually configured as a programmable or memory-programmable unit configured for programming, for example, in the form of a microprocessor (μP), microcomputer, microcontroller (μC) or in a comparable form of a memory-programmable controller (MPC) or of a programmable logical unit (ASIC, FPGA, PAL, GAL). The memory unit is configured with components for data storage and data supply, which are usually configured in the form of volatile or non-volatile memory units (RAM, ROM, EEPROM) or removable data storage media (SD card, CF card, USB stick). Furthermore, the gas-measuring device according to the present invention, preferably the output unit, may have at least one optical interface for connecting the gas-measuring device to additional devices or components.

The operating unit is configured and intended for making orientation in space possible for a user in at least one detection area in the measuring environment and thus to define the detection area in terms of position and size in the measuring environment by the operating unit offering the user a possibility of selecting the spatial position of the detection area.

The control unit is configured for controlling the first camera such as to initiate the detection of image information within the at least one detection area and to store the detected image information as first image data in a first image data set of the memory unit.

The control unit is further configured to control the second camera such as to initiate the detection of image information in the detection area and to store the detected image information as second image data in a second image data set of the memory unit.

The control unit is configured, in interaction with the memory unit, by means of a data processing of the first and second image data sets, to determine and to mark special image areas, which indicate contours or outlines of individual persons or of a plurality of persons as well as individual persons or a group of persons, and to arrange them as marked data in the first image data set. The marking may be carried out, for example, by means of addressing data or data areas in the memory unit.

The control unit is further configured to determine at least one gas concentration of a gas or of a gas mixture in the measuring environment on the basis of the first image data set, taking into account the marked data in the first image data set, and to make it available to the output unit.

The output unit is configured to provide or output an output signal, which indicates the at least one determined gas concentration.

In summary, the device according to the present invention for detecting an invisible image area in the measuring environment by means of the first camera and by means of the detection of a visible image area in the measuring environment by means of the second camera makes possible the interaction of the control unit, operating unit, output unit and memory unit such that the operating unit makes orientation possible for the user in at least one detection area in the measuring environment, the control unit controls the first camera and the second camera such as to detect image information in the visible range and in the invisible range and to store the image information as image data sets in the memory unit, the control unit determines, in interaction with the memory unit, special image areas, which indicate contours or outlines of individual persons or of a plurality of persons as well as individual persons or a group of persons, the control unit marks, in interaction with the memory unit, the determined special image areas, which indicate contours or outlines of individual persons or of a plurality of persons as well as individual persons or a group of persons, and the control unit determines at least one gas concentration of a gas or of a gas mixture in the measuring environment, taking into account the marked data, and the output unit provides or outputs, in interaction with the control unit, an output signal, which indicates at least one determined gas concentration.

The spatial orientation of the at least one detection area in the measuring environment is effected such that one operating element or a plurality of operating elements, by means of which the user is able to select an image detail in the measuring environment, is/are arranged in or at the operating unit, or one operating element or a plurality of operating elements is/are associated with the operating unit. Functions that are necessary for this for selecting the image detail in the measuring environment, for example, a part of an industrial area or an industrial plant, e.g., image focusing and image magnification as well as settings of contrast, brightness, color selection and color adjustment, are typically carried out by means of operating or setting elements (arrow keys, rotary knobs, push-buttons, touch screen displays).

After selecting the image detail, the control of the first and second cameras is then carried out continuously by means of the control unit, so that images of the two cameras are detected and stored as image data in the first image data set and the second image data set in the memory unit.

The special image areas determined are marked in the first image data set by the control unit after the determination on the basis of the image data of the first and second cameras. The marking of the special image areas may be carried out, for example, by means of sorting, addressing or readdressing of data or data areas within the memory unit. The special image areas can preferably be described by coordinates in the image detail. Suitable coordinate systems are, for example, a Cartesian coordinate system or a polar coordinate system referenced to the image center of the image detail.

The determination of the special image areas is carried out by means of mathematical and statistical methods, as they are described, for example, in U.S. Pat. No. 6,130,964 B (the entire contents of U.S. Pat. No. 6,130,964 B are incorporated herein by reference). The method explained and used there determines the image areas in the image detail that indicate individual persons or contours thereof, as well as a plurality of persons or contours thereof, in the manner described below. Space-related and time-related information are included in a double partition approach for a two-time segmentation, and after a first classification to objects, for example, persons, this information is then segmented once again. This increases the accuracy of the segmentation and makes it also possible to segment inhomogeneously moving and static objects. Contours of persons have typical circumferential shapes of human bodies with head, trunk, arms and legs, which represent a physiological characteristic for human body shapes for a frontal profile and/or a lateral profile. However, clothing elements and equipment items, such as helmets or respirators carried on the back, may also be included in the contours in the frontal profile and/or lateral profile as technical characteristics, so that a combination of physiological characteristics and technical characteristics is obtained. In addition, the orientation of the persons, such as upright or bent forward in the upright position, walking, squatting, may supplement the physiological characteristic.

In a preferred embodiment, the marked data in the first image data set are taken into account by the control unit by means of a replacement of the marked data in the first image data set by equivalent data.

The equivalent data may be formed or determined in different manners and thus they may be used by the control unit in different manners when taking into account the special image areas and/or the marked data.

The equivalent data may be configured or be able to be determined according to a least one of the following variants, so that
- the equivalent data are based on data that do not belong to the special image area,
- the equivalent data may be configured as static equivalent data, which are not based on current data from the actual measuring environment,
- the equivalent data are not based on current data from the measuring environment,
- the equivalent data are based on data of the first image data set, which represent areas of an immediate area surrounding the special image area in the measuring environment, and
- the equivalent data can be determined from data of the first image data set, which represent areas of an immediate area surrounding the special image area in the measuring environment.

The replacement of the equivalent data in the first image data set may preferably be carried out by the image elements (pixels) of the special image area in the first image data set being replaced by equivalent data (replacement data) quasi pixel by pixel.

The equivalent data are preferably configured here as static equivalent data, which are not based on data from the actual measuring environment. This could be done, for example, by setting the values at a value of zero or at a maximum.

Such an approach could lead, due to the principle, to an underestimation or overestimation of the gas concentration, and this could happen differently depending on the spatial extension of the persons or of the group of persons in relation to the spatial extension of the gas cloud.

In another preferred embodiment, the equivalent data are determined by the control unit from data of the first image data set. These data do not belong to the special image area and represent areas in the immediate area surrounding the special image area. The immediate area surrounding the special image area can preferably be described, in the same manner as the special image areas, by coordinates in the image detail. Suitable coordinate systems are, for example, a Cartesian coordinate system or a polar coordinate system referenced to the image center of the image detail.

The entire image shall be designated by the set I, and the special image area, i.e., the segmented persons in the field of view, by the set A. The equivalent data (replacement data) A' for the pixels in the special image area A are then, for example, data in the immediate area surrounding the special image area A.

For example, the pixels in the special image area may be replaced by the maximum or minimum of the surrounding values, so that they are not also located in the special image area.

It follows for the replacement data according to the following formula 1:

$$A' = \left\{ \text{Pixel } x \in A \mid x = \max(w_1 * x_1, \ldots, w_n * x_n), \text{ für } w_1, \ldots, w_n \in \mathbb{R}, \text{ for } x_1, \ldots, x_n \in \frac{1}{A} \cdot \begin{bmatrix} x_1 & \ldots & x_{\frac{n}{3}} \\ \ldots & x & \ldots \\ x_{\frac{2n}{3}} & \ldots & x_n \end{bmatrix} \right\}$$

The number of the surrounding values used to calculate the equivalent data, i.e., the size n of the matrix being considered around the value x to be replaced, as well as a possible weighting $w_i$ of the values of this matrix can be adapted here to the contrast of the cameras. An approach according to this other preferred embodiment, in which the minimum or maximum is taken into account, may also lead to an underestimation or overestimation of the actual gas concentration. However, the effect of the underestimation or overestimation of the actual gas concentration is markedly less severe than in case the equivalent data are configured with values of zero or the maximum value.

Furthermore, a mean value may also be used instead of the maximum in another preferred embodiment. The most accurate values concerning a spatial (not temporal) equivalent parameter can be obtained in this case. The equivalent data may preferably also be determined on the basis of arithmetic or root mean square mean values, median values, as a sliding mean value or the like.

The advantage of this method is the short calculation time, because only data from the current image detail must be used in this case.

The immediate area U surrounding the special image area, i.e., the immediate area surrounding a contour of a person or of a contour of a group of persons can be described here as follows:

$$U = \{\text{Pixel } x \in I/A | \text{dist}(x,A) < m, \text{dist}(x,A) = \min_{a \in A}(x,a)\} \quad \text{Formula 2}$$

The size of the surrounding area may, of course, be adapted in this case as well. Care should be taken, in particular, to ensure that the selected matrix size n in Formula 1 fits the selected distance m.

In another preferred embodiment, the equivalent data are determined by the control unit from data that were detected at a previous time by means of the first camera and were stored in a fourth image data set.

The data detected at a previous time are data whose image elements (pixels) do not indicate any person or persons or contours of individual persons or of a plurality of persons. These previous data indicate essentially a previous situation of the measuring environment without the presence of persons in the area of the image detail of an essentially spatially identical position of the measuring environment.

The suitable previous data are data of a background image recorded during the putting into operation of the gas-measuring device, which background image is scaled to a fixed point. The background image recorded during the putting into operation is typically used to compensate differences in the outside temperature.

Formula 3 is obtained for the image $I_N$ at a previous time:

$$I_N' = \{\text{Pixel } x \in I_N | x = c*x, c \text{ scale factor}\} \qquad \text{Formula 3}$$

The scale factor c is obtained here from the quotient of the pixel values of $I_N$ and I at a previously set fixed point to compensate the change in the surrounding area. This previously set fixed point is quasi a point before a static background, which is exposed to changes in the surrounding area, for example, changes in sunlight.

For the equivalent data (replacement data) the result is:

$$A' = \{\text{Pixel } x \in A | x = x_N, x_N \in I_N'\}. \qquad \text{Formula 4}$$

The advantage of this embodiment is that the change over time is taken into account and structures that are located behind the segmented persons are taken into consideration. The concentration determination becomes much more simple and accurate as a result. However, a gas cloud may also not be imaged in some cases if it was not yet present in the image at the previous time being considered. This possibly leads to an underestimation of the measuring environment, i.e., also of the gas concentrations determined in the measuring environment.

Suitable previous data are data of a time interval or of a time preceding in time the time at which persons were detected in the field of view, likewise scaled to a fixed point. For example, a duration of a few seconds may be selected as a typical time interval for a situation immediately before the time at which persons were detected in the visible area. The composition and the concentration of a gas mixture in the measuring environment or in the image detail was advantageously similar during this duration as at the time of or after the entry or presence of persons in the image detail or in the measuring environment.

In another preferred embodiment, the pixels from the special image area are replaced with the last pixel or by a combination of the last pixels, when the pixel or pixels did not yet belong to the special image area.

For example, $$A' = \{\text{Pixel } x \in A | x = \max(x_1, \ldots, x_n), x_i \in I_i', i=1, \ldots, n, x_i \notin A_i\} \qquad \text{Formula 5}$$

is obtained for the maximum operator.

For example, $$A' = \{\text{Pixel } x \in A | x = \min(x_1, \ldots, x_n), x_i \in I_i', i=1, \ldots, n, x_i \notin A_i\} \qquad \text{Formula 6}$$

is obtained for the minimum operator.

For example, $$A' = \{\text{Pixel } x \in A | x = \text{mean}(x_1, \ldots, x_n), x_i \in I_i', i=1, \ldots, n, x_i \notin A_i\} \qquad \text{Formula 7}$$

is obtained for the mean value operator.

As is shown in Formula 7, the equivalent data can preferably also be determined on the basis of arithmetic or root-mean-square mean values, median values, as a sliding mean value or the like from data of any desired time interval.

Furthermore, the number n of times taken into account in the past as well as a possible weighting c of the times are variable, and the data that were detected in the typical time interval close in time to the current time are preferably included in the equivalent data with more weight than are data that were detected in the typical time interval farther away in time from the current time.

$$A' = \left\{ \begin{array}{l} \text{Pixel } x \in A \mid x = \text{mean}(c_1 * x_1^1, \ldots, c_n * x_1^p), \\ c_i \in \mathbb{R}; x_1^i \in \dfrac{I_i'}{A_i}, i = 1, \ldots, p \end{array} \right\} \qquad \text{Formula 8}$$

The advantage of this embodiment is that the comparison values are in the more recent past and the chances that the equivalent data also include the possible gas cloud are thus greater.

In another preferred embodiment, the equivalent data are obtained from a combination of the determination of equivalent data in time and space, i.e., in reference to the preceding embodiment, not only the values at the respective pixel to be replaced are taken into account at the previous times, but the pixels surrounding those pixels are taken into account at the previous times as well.

This embodiment is probably the most accurate possibility of calculating equivalent data, because both time- and space-related information is used to generate the equivalent data.

The corresponding Formula 9 is obtained from the above considerations as follows:

$$A' = \left\{ \begin{array}{l} \text{Pixel } x \in A \mid x = \max\left(w_1 * \sum_{i=1}^{p} c_i * x_1^i, \ldots, w_n * \sum_{i=1}^{p} c_i * x_n^i\right), \\ \text{for } w_1, \ldots, w_n, c_1, \ldots, c_n \in \mathbb{R}, \text{ for } x_1^i \in I_i' \Big/ A_i \begin{bmatrix} x_1 & \ldots & x_{\frac{n}{3}} \\ \ldots & x & \ldots \\ x_{\frac{2n}{3}} & \ldots & x_n \end{bmatrix} \end{array} \right\}$$

In another preferred embodiment, the control unit is configured to replace the marked data in the first image data set by equivalent data and to generate a third data set (a further data set) from the first image data set and the equivalent data. This additional preferred embodiment represents a special variant of the embodiment according to the present invention, in which not only are these special image areas marked and taken into account in the first image data set during the concentration determination, but a common image data set is generated in the third image data set from equivalent data and the unmarked data of the first image data set, which common data set is suitable for the further determination of the at least one gas concentration of the gas or gas mixture in the measuring environment, in which case a continuous updating is then made possible in the first image data set in reference to changes concerning both motions of gases and changes of structural components (ladders, scaffolding, pipelines) in the image detail and/or in the measuring environment. This makes possible a concentration determination that not only takes into account the persons present, but actually uses equivalent data that simulate how it is (the state) behind the persons present.

The control unit is configured in another preferred embodiment to determine a gas concentration of the gas or gas mixture in the measuring environment on the basis of the third image data set. The determination of the gas concentration on the basis of the first image data set and/or of the third image data set may be carried out such that the ratio of measurement results is taken into account. The measurement result is, on the one hand, a measurement result from a wavelength range in which the gas is not active. Both measurement results are corrected by the control unit with the background.

These measurement results may be determined by different technical aspects. The determination of gas species and gas concentrations is carried out in, for example, U.S. Pat. No. 6,803,577 B by means of spectral data, which are recorded simultaneously by two cameras, filtering in the process through a cell filled with the target gas(the entire contents of U.S. Pat. No. 6,803,577 B are incorporated herein by reference). The concentration is then obtained from the ratio of the measured values to the concentration in the gas cell, which was used for the filtering. A camera is used together with different filters in U.S. Pat. No. 7,977,639 B (the entire contents of U.S. Pat. No. 7,977,639 B are incorporated herein by reference). The necessary images consequently develop one after another. The concentration determination is based here on the ratio to an existing set of parameters.

The analysis unit is configured in this additional preferred embodiment to provide or output an output signal, which indicates the at least one determined gas concentration, on the basis of the third image data set.

The output unit is configured in another preferred embodiment to provide or output a control signal, which represents an equivalent image of the measuring environment, on the basis of the third image data set. The special image areas are replaced in this equivalent image according to this additional preferred embodiment by equivalent data such that no information on persons or groups of persons is contained in the invisible image data, but an attempt is made, instead, to simulate the thermographic or spectral situation instead of the persons.

For better visualization, the detected visible image information is superimposed to the third image data set in another preferred embodiment, and even though the persons can be seen in the visible part as, for example, a contour, the superimposed spectral information represents the gas cloud or the concentration distribution in the gas cloud rather than the persons themselves. The superimposition of detected spectral image information from the invisible optical area to the detected visible image information is performed, for example, by means of prior-art image processing methods, as described, for example, in U.S. Pat. No. 8,755,597 B or U.S. Pat. No. 8,520,970 B (the entire contents of U.S. Pat. Nos. 8,755,597 B and 8,520,970 B are incorporated herein by reference). As a first step, the resolution and the visible area are adapted by a coordinate transformation in order for the details to be ultimately also superimposed at the correct location. The superimposition is carried out here such that the visible image of the second camera is processed by means of a high-pass filtering and the invisible infrared image of the first camera is processed by means of a low-pass filtering, and the filtered data are subsequently combined into one image.

For better visualization, the detected visible image information is superimposed to the third image data set in another preferred embodiment, so that persons are represented not only in the visible part of the superimposition, but the contours of individual persons or contours of a plurality of persons are also represented as a contour or linear shape. The superimposition is effected here as was described above. The contours of the special areas A are determined and are also represented in the equivalent image after a coordinate transformation.

In another preferred embodiment, the control unit is configured to detect one or more pieces of marking information arranged on the individual persons or on a plurality of persons and to store the one or more pieces of marking information in a marking data set. Such marking elements may be configured, for example, as letterings or marks on the work clothes or distinctive personal safety products in the visible area. Marking elements may be configured, for example, as part of the clothes or components arranged on the clothes or on the protective helmet of the person or persons, which may be fastened on the clothes by means of Velcro fastener, snap fasteners, magnetic connections, bonded connections, safety pins, clips or specially configured locking elements or docking connections (quarter-turn fastener). The marking may have various shapes and/or colors and indicate different individual persons or indicate different groups of persons (maintenance teams, assembly teams, visitors) by the shape and/or color. It is also possible, for example, to use for the marking active markers, for example, IR-LEDs, which are also detectable in the invisible area and are then also present as data in the first image data set. The detection of individual persons or of a plurality of persons is carried out here by means of prior-art image processing methods, as described, for example, in U.S. Pat. No. 7,769,236, and the marking to be expected in the image is searched for and found in the image by means of an edge detector and is then compared to the properties of the marking to be expected, and it can be assigned to defined persons or groups of persons corresponding to the properties (the entire contents of U.S. Pat. No. 7,769,236 are incorporated herein by reference).

An edge detector that can possibly be used is described in U.S. Pat. No. 8,300,949 B2 (the entire contents of U.S. Pat. No. 8,300,949 B2 are incorporated herein by reference). After suitable filtering to accentuate high frequencies, the image is scanned in the horizontal and vertical directions for great differences in intensity. Edges can also be found in this original image at these locations.

In another preferred embodiment, the control unit is configured to determine at least one identification signal that can be assigned to an individual person on the basis of the marking data set and of the first, second or third image data set. The output unit is configured in this additional preferred embodiment to output the equivalent image representing the measuring environment on the basis of the identification signal and of the control signal. A marking information that can be assigned to the at least one person is faded into, integrated in or superimposed to the equivalent image by means of the identification signal. This fading in or superimposition may be configured, for example, in the form of a characteristic as an alphanumeric code, initials, as a real name or as a photo of the person or the like.

The fading in or superimposition of marking information is carried out here, for example, by means of prior-art image processing methods, as it is described, for example, in EP 0443064 (the entire contents of EP 0 443 064 (B1) are incorporated herein by reference). The fading in or superimposition is carried out here by means of visible image elements (pixels), which are indicated by marking elements, in the following manner such that the marked image area is replaced by a previously defined second image, taking care to ensure a reasonable contrasting compared to the initial image in order to improve the visualization.

The embodiments described represent special embodiments of the gas-measuring device according to the present invention each in itself as well as in combination with one another. All the additional embodiments arising from a combination or combinations of a plurality of embodiments as well as their advantages are nevertheless also covered by the inventive idea, even if not all the possibilities of combinations of embodiments are described for this in detail.

The controls, data operations, data manipulations, calculations, analyses and provisions of outputs described in the described embodiments of the control unit may also be configured as a process, preferably as a computer-implemented process. The control unit may be configured in the form of hardware components (FPGA, ASIC, GAL) or of one or more processors (µC, µP, DSP) in order to process instructions for carrying out controls, data operations, data manipulations, calculations, analyses and the provision of outputs, which may be implemented in a memory area.

The present invention will be explained in more detail by means of the following figure and of the corresponding description of the figure without limitation of the general inventive concepts. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 1 is a schematic view of an infrared optical gas-measuring device.

DESCRIPTION OF PREFERRED EMBODIMENTS

Referring to the drawings, FIG. 1 shows in the schematic view an infrared optical gas-measuring device 1 with a first camera 3 and with a second camera 5 as well as with a control unit 13, with a memory unit 15, with an operating unit 17 and with an output unit 19 in a measuring environment 7, in which one or more persons 9 are present. The control unit 13 is intended for controlling the gas-measuring device 1, especially the cameras 3 and 5, as well as for the data analysis of signals detected by means of the cameras 3 and 5, and has for this a computer (µC) 13' and a working memory (RAM) 13".

Furthermore, an operating unit 17 is provided, in which operating elements 17' are arranged in order to enable a user to set up and orient the device 1 for the gas measurement with the cameras 3, 5 in a spatial scenario. This set-up or orientation of the cameras 3, 5 defines an invisible image area 33, which is detected by means of the first camera 3, and a visible image area 55, which can be detected with the second camera 5. The image areas 33, 55 yield in their overlap a detection area 11. The user can then select the spatial orientation 11' of the detection area in the measuring environment 7. This may be carried out, for example, such that the cameras 3, 5 are rotated or pivoted by a manual or motor-driven motion.

The control unit 13 is configured here to control both the first camera 3 and the second camera 5 as well as to detect invisible image information (image information in infrared spectral range) 33' of the invisible image area 33 by means of the first camera 3 as well as visible image information 55' of the visible image area 55 by means of the second camera 5. The control unit 13 is configured, in interaction with the memory unit 15, for the data processing of the detected image information 33' and 55'. The visible image information 55' is stored during this interaction as visible image data 53' in a second image data set 53 of the memory unit 15. Furthermore, the invisible image information 33' is stored during this interaction as invisible image data 35' in a first image data set 35 of the memory unit 15. The interaction of the memory unit 15 and the control unit 13 makes it furthermore possible to identify special image areas 66 from the first image data set 35 and the second image data set 53 by means of a data processing. These special image areas 66 indicate persons or contours of individual persons 9, of a plurality of persons 9, who are present in the detection area 11. These special image areas 66 are arranged as marked data 66' in the first image data set 35. Based on the first image data set 35 with the marked data 66', the control unit 13 is then able to determine at least one gas concentration 21' of a gas or of a gas mixture in the measuring environment 7 in the detection area 11. The at least one gas concentration 21' of the gas or gas mixture is provided or outputted as an output signal 21 by means of an output unit 19, which is associated with the control unit 13 or is arranged in the control unit 13. The output signal 21 indicates here the at least one gas concentration 21' of the gas or gas mixture in the measuring environment 7 or in the detection area 11. For example, a visual representation 23 can be generated or provided by means of the output signal 21. The visual representation 23 may represent here the visual image data 53' such that they are viewed together with the gas concentration 21' in a graphic form. The marked data 66' are used in the control unit 13 to replace in the special image areas 66 the pixels that can be assigned to persons 9 by equivalent data 37. Especially data from the first image data set 35, which do not belong to the special image area 66 and represent areas of an immediate area surrounding these special image areas 66 in the measuring environment 7, are determined as equivalent data 37 from the first image data set 35. These are thus, for example, detected data of the first image data set 35, which represent, so to speak, a gaseous envelope or envelope of the persons 9 in the measuring environment 77. An alternative to generating the equivalent data is given if the persons 9 are moving in the measuring environment 7. Data from the first image data set 35, which were detected at a previous time, when no persons 9 were present at this spatial position in the measuring environment 7, can be used in such a case. It is more preferable to copy or shift these data of the previous time from the first image data set 35 for the further processing into a fourth image data set 41 within the memory unit 15 for use as equivalent data 37.

The control unit 13 is configured to determine a third image data set 39 from the first image data set 35 and the equivalent data 37 and to determine the at least one gas concentration 21' of the gas or gas mixture in the measuring environment 7 on the basis of this third image data set 39. The output unit 19 is configured now to determine and provide on the basis of the third image data set 39 an output signal 21, which represents an equivalent image 57 of the measuring environment, in which visible image information 53 and invisible image information 33' are represented overlapped for easier orientation. The areas in which persons 9 determine the image are replaced by equivalent data 37 in the invisible part of this equivalent image 57. It is shown in this FIG. 1 that the persons are also contained in a linear shape 9' in the visual representation 23 in this equivalent image 57. Provisions may be made in a special configuration for marking elements 8 to be arranged, for example, on the clothes, on the persons 9 in the measuring environment 7. Either the first camera 3 or the second camera 5 or both cameras 3, 5 may be able by means of these marking elements to identify persons 9 in the image. The marking element 8 may be configured for such an identification, for example, in the form of a significantly visible element, for example, in color or by a graphic structuring (QR code). It is then also possible by means of these marking elements 8, which are arranged on the persons 9, to make identifiable the persons 9 in the equivalent image 57 of the visual representation 23 by means of identification signals 8' derived from the marking elements 8 instead of as contours 9'. The identification signals 8' may be used here both instead of a contour representation 9' as well as in addition to the contour representation 9' in the visual representation 23.

FIG. 1 shows an operating unit 17, which has some operating elements, which are suitable for controlling and orienting the cameras 3, 5. A user is able in this manner to adapt the detection area 11 to the particular situation in the measuring environment 7 in terms of both the visible image area 55 and the invisible (to the human eye) image area 33. Such an adaptation of the cameras 3, 5 to the situation of the measuring environment 7 may be carried out, for example, by persons 9 moving in the measuring environment 7, so that movements 99 of persons occur in front of the detection areas 11, 33, 55. A movement 99 of persons 9' can then also be provided as a graphic representation by means of the visual representation 23 by using marking elements 8 arranged on the persons 9. The movements 99 of persons can thus be used to obtain marking information 88, which is assigned to individual persons or to a plurality of persons 9. A marking data set 88', with which the movement 99 of a person in the measuring environment 7 or in the detection area 11 over certain time periods, for example, during the duration of a work assignment of the persons at the location of the measuring environment 7, can be stored in the memory unit 15, can advantageously be obtained from the marking information 88.

In addition to the output of the output signal 21 to the visual representation 23, an interface 19' is also arranged in the control unit 13 in order to make the results of the image data analysis of the two cameras 3, 5 available by means of a control signal 56 outside the device 1. The control signal 56 may be fed, for example, into a data network, which can display the information 8', 9', 53', 21' in a wired or wireless manner at a location different from the measuring environment 7 and the work assignment location of the person 9, for example, at a remote monitoring station in an industrial plant, on a monitor arranged there.

While specific embodiments of the invention have been shown and described in detail to illustrate the application of the principles of the invention, it will be understood that the invention may be embodied otherwise without departing from such principles.

APPENDIX: LIST OF REFERENCE NUMBERS

1 Gas-measuring device
3 First camera (IR)
5 Second camera
7 Measuring environment, gas cloud
8 Marking element
8' Identification signal
9 Persons
9' Linear shape
11 Detection area
11' Spatial orientation
13 Control unit
13' Data processing components
14 Camera control signals
15 Memory unit
17 Operating unit
17' Operating elements
19 Output unit
19' Interface
21 Output signal
21' Gas concentration
23 Visual representation
33 Invisible image area
33' Invisible image information
35 First image data set
35' Invisible image data
37 Equivalent data
39 Third image data set
41 Fourth image data set
53 Second image data set
53' Visible image data
55 Visible image area
55' Visible image information
56 Control signal
57 Equivalent image (visible and invisible)
66 Special image areas
66' Marked data
77 Motion of gas cloud
77' Local/spatial changes of the gas cloud
88 Marking information
88' Marking data set
99 Movements of persons

What is claimed is:

1. A gas measurement device for gas measurement in a measuring environment, the gas measurement device comprising:
   a first camera configured for detecting an invisible image area in the measuring environment;
   a second camera suitable for detecting a visible image area in the measuring environment;
   an operating unit configured to provide a spatial orientation of at least one detection area in the measuring environment for a user;
   a memory unit;
   a control unit configured to control the first camera including initiating a detection of invisible image information within the at least one detection area and to store the detected image information as first image data in a first image data set of the memory unit and configured to control the second camera including initiating a detection of visible image information in the at least one detection area and to store the detected image information as second image data in a second image data set of the memory unit and configured to interact with the memory unit by means of a data processing of the first and second image data sets to determine and to mark special image areas, which special image areas indicate individual persons or a plurality of persons or contours of individual persons or contours of a plurality of persons, and to arrange the special image areas as marked data in the first image data set and is configured to determine at least one gas concentration of a gas or of a gas mixture in the measuring environment on the basis of the first image data set including the marked data; and
   an output unit configured to provide or output an output signal, which indicates the at least one determined gas concentration.

2. A gas measurement device in accordance with claim 1, wherein the special image area or the marked data or both the special image area or the marked data are taken into account by the control unit by means of a replacement of the marked data in the first image data set with equivalent data.

3. A gas measurement device in accordance with claim 2, wherein the equivalent data is configured or determined in accordance with at least one of the following variants:
   the equivalent data are based on data that do not belong to the special image area;
   the equivalent data are configured as static equivalent data, which are not based on data from the actual measuring environment;
   the equivalent data are not based on current data from the measuring environment;
   the equivalent data are based on data of the first image data set, which represent areas of an immediate area surrounding the special image area in the measuring environment; and
   the equivalent data is calculated based on data of the first image data set, which represent areas of an immediate area surrounding the special image area in the measuring environment.

4. A gas measurement device in accordance with claim 2, wherein:
- the equivalent data are determined by the control unit based on a further image data set;
- the further image data set indicates essentially a previous situation of the measuring environment or a combination of a plurality of previous situations of the measuring environment without the presence of persons in an area of the image detail of a spatially essentially identical position of the measuring environment.

5. A gas measurement device in accordance with claim 2, wherein:
- the control unit is configured to generate a further image data set from the first image data set and the equivalent data of a third image data set;
- the control unit is configured to determine the at least one gas concentration of a gas or of a gas mixture in the measuring environment on the basis of the further image data set; and
- the output unit is configured to provide or to output an output signal, which output signal indicates the at least one determined gas concentration, on the basis of the third image data set.

6. A gas measurement device in accordance with claim 5, wherein the output unit is configured to provide or output a control signal, which control signal represents an equivalent image of the measuring environment, on the basis of the further image data set.

7. A gas measurement device in accordance with claim 6, wherein the equivalent image is configured as a superimposition of the detected invisible image information to the detected visible image information, so that the persons or the contours of persons are not visible in the equivalent image.

8. A gas measurement device in accordance with claim 6, wherein the equivalent image is configured as a superimposition of invisible image information to detected visible image information, so that the contours of individual persons or contours of a plurality of persons are represented as an outline or linear shape in the equivalent image.

9. A gas measurement device in accordance with claim 6, wherein:
- the control unit is configured to process the first image data set or the second image data set or both the first image data set and the second image data set to detect marking elements arranged on the individual persons or on a plurality of persons and to store one or more pieces of marking information in a marking data set;
- the control unit is configured to determine at least one identification signal that can be assigned to an individual person on the basis of the marking data set; and
- the output unit is configured to output the equivalent image representing the measuring environment on the basis of the identification signal and of the control signal.

10. A gas measurement device in accordance with claim 1, wherein the control unit is configured to process the first image data set or the second image data set or both the first image data set and the second image data set to detect marking elements arranged on the individual persons or on a plurality of persons and to store one or more pieces of marking information in a marking data set.

* * * * *